United States Patent [19]

Thompson et al.

[11] 4,111,827

[45] Sep. 5, 1978

[54] AEROSOL FOAMS

[75] Inventors: John Thompson, Maidenhead; Adrian Pitfield, High Wycombe, both of England

[73] Assignee: Wilkinson Sword Limited, England

[21] Appl. No.: 662,265

[22] Filed: Feb. 27, 1976

[30] Foreign Application Priority Data

Feb. 27, 1975 [GB] United Kingdom ............... 8249/75

[51] Int. Cl.$^2$ ............................................. C11D 17/00
[52] U.S. Cl. ..................................... 252/90; 252/305; 252/307; 252/DIG. 7; 252/DIG. 13; 252/DIG. 14; 424/73
[58] Field of Search ......... 252/90, 305, 307, DIG. 13, 252/7, 14; 424/73

[56] References Cited

U.S. PATENT DOCUMENTS

| | | | |
|---|---|---|---|
| 3,705,858 | 12/1972 | Marschner | 252/90 |
| 3,715,942 | 2/1973 | Courtney | 252/90 X |
| 3,719,752 | 3/1973 | Taylor | 252/305 X |
| 3,959,160 | 5/1976 | Horsler et al. | 252/90 |

*Primary Examiner*—Mayer Weinblatt
*Attorney, Agent, or Firm*—Birch, Stewart, Kolasch and Birch

[57] ABSTRACT

Aerosol shaving foam preparations are disclosed containing as the foamable medium an aqueous concentrate containing a selected, nitrogen-containing surfactant, a long chain alcohol and a third surfactant component, preferably a water-soluble nonionic surfactant.

5 Claims, No Drawings

AEROSOL FOAMS

FIELD OF THE INVENTION

This invention relates to pressurized shaving foam dispensers of the so-called aerosol type, and more particularly to the formulation of the foamable compositions used therein.

BACKGROUND OF INVENTION

In pressurized shaving foam dispensers of the above-mentioned type, a foamable concentrate, generally an aqueous soap solution, is contained in a dispenser equipped with a dispensing head and valve, and pressurized with a normally gaseous propellant, e.g., a low molecular weight hydrocarbon or hydrocarbon mixture, or a halohydrocarbon or halohydrocarbon mixture. In the container the liquefied propellant forms an emulsion in the foamable concentrate, the emulsion being referred to as an aerosol emulsion. Upon discharge of the emulsion through the dispensing head the volatilization of the dispersed liquid droplets of propellant causes the dispensed concentrate to foam. Depending upon the precise formulation of the concentrate, the dispensed product may range from a dense creamy foam to a light lather.

For the avoidance of doubt, the term "emulsion" will be used throughout this specification to refer to the whole liquid contents of the dispenser, i.e., the foamable concentrate plus liquid phase propellant, and the term "concentrate" will be used to refer to the liquid content of the dispenser, other than the propellant, "liquid" in this context embracing solutions, emulsions and suspensions. In other words, the concentrate itself may be an emulsion or suspension and not necessarily a solution of the foam producing ingredients in a suitable liquid medium, which in the case of the present invention will be water.

Various disclosures have been made of compositions suitable for use in such dispensers, amongst which may be mentioned U.K. patent specification No. 838,913 and U.S. Pat. No. 2,655,480. In accordance with the proposals of U.K. patent specification No. 838,913 aqueous soap solutions are used in which the quantity of alkali metal ammonium or alkylamine soaps, or soaps of primary or secondary alkanolamines, is kept below 4%, based on the weight of the concentrate, and in which the amount of triethanolamine soap is kept in minor proportion relative to the total soap content. In accordance with U.S. Pat. No. 2,655,480 aqueous soap solutions are also used, the actual concentration varying with the particular soap used. Thus, when triethanolamine stearate is used the concentration may be from 2–30% by weight of the solution and when potassium stearate is used the recommended amount is from 5 to 20%. A generally recommended range for all soap is 5 to 18%.

Yet other aqueous soap solutions are disclosed in U.S. Pat. No. 2,908,650, these being aqueous solutions of alkali metal soaps and soaps of nitrogen bases in specified proportions.

In such prior compositions a variety of additives have been proposed or used to modify or control the properties of the foam or emulsion. For example, U.S. Pat. No. 2,655,480 discloses that water-soluble non-ionic wetting agents may be added in amounts up to 5 or 6%, based on the weight of the concentrate, to facilitate rinsing of the lather from the face and avoiding oily deposits on the skin. Particular anionic and non-ionic wetting agents mentioned are sodium lauryl sulphate, sodium dodecyl benzene sulphonate, and water-soluble polyoxyethylene ethers of alkyl-substituted phenols. In addition, glycerine may also be added to stabilize the lather. U.K. patent specification No. 838,913 discloses the addition of small amounts (1–3%) of water-soluble emulsifiers, e.g., fatty acid alkanolamides. U.K. Pat. No. 838,913 also discloses the addition of water-insoluble fatty acids, fatty alcohols and their ethylene oxide derivatives, to give the lather a creamy character and effect a slight fatting of the skin. In addition, U.K. Pat. No. 838,913 further teaches the addition of relatively high amounts (up to 15%) of water-insoluble free fatty acid to effect stabilization of the lather.

Reference may also be made to the studies reported in J. Soc. Cosmetic Chemists, 17 (1966), pages 801–830 on the effects of the addition of long chain fatty alcohols to aqueous aerosol emulsions based on anionic surfactants, in particular on certain triethanolamine soaps and on sodium lauryl sulphate. In general, the addition of long chain alcohols to these emulsions showed an increase in viscosity and emulsion stability, judged on the time required for phase separation after shaking the aerosol container by hand. Increases were also noted in foam stability and foam stiffness.

Although soap-based aerosol shaving foams have attained a certain degree of popularity, the formulations currently used have certain disadvantages, the foremost of which is the tendency, when used, to form a scum either in the form of hardwater deposits, particularly, of course, when used in hard water areas, or in the form of free fatty acid. This scum, in turn, forms unsightly deposits around the wash basin and, more particularly, on the razor and because of the difficulty of removing these deposits, which are often not removed by simple rinsing, the razor rapidly becomes encrusted.

Soapless aerosol foams based on synthetic surfactants and containing a synthetic surfactant in combination with a long chain fatty acid or alcohol have been described. For example, in Soap and Chemical Specialities, July 1967, pages 70–78 and 162, continued in Soap and Chemical Specialities, August 1967, pages 70–74, 104 and 106, and in J. Soc. Cosmetic Chemists 20, (August 1969) 577–593, Sanders describes a series of studies on aerosol emulsion systems based on certain polyethylene fatty ethers in combination with certain long chain fatty acids and alcohols. Again, increases in emulsion viscosity and stability and increases in foam stability and stiffness were noted. Whilst, since such systems are soap free, the problem of hard water scum does not arise, it has been found that such systems have a particular disadvantage in that they lack storage stability, particularly at moderately elevated temperatures, e.g., 30°–40° C., which in practice may well occur when the products are stored or placed on display, for example, in a shop window exposed to bright sunlight or are used in a hot climate. Under these exposed conditions, compositions containing a synthetic surfactant solution and a long chain fatty alcohol or acid, as described in these articles, undergo an irreversible phase separation, that is to say they cannot be redispersed merely by shaking the aerosol container by hand, with the result that the emulsion no longer foams, or foams inadequately upon discharge from the container. Such products therefore lack the necessary shelf-life. In addition, separated solid phase material may block the valve and discharge apertures and thus further contribute to the malfunction of the container.

In our U.K. patent specification No. 1,423,179 and the corresponding German application published as OLS P No. 24 22 937.6 there are disclosed aerosol shaving foam preparations comprising a particular combination of surfactant materials, such preparations having the advantageous properties of not only being free from scum formation when used in hard water, but also having the ability to disperse preformed scums, which result, for example, when the face is washed with ordinary soap under hard water conditions prior to shaving. Furthermore, these preparations are stable at moderately elevated temperatures, e.g., 30°–40° C., for long periods. Broadly speaking, such preparations are based on an aerosol emulsion containing as the surfactant a combination, in particular proportions, of (i) a water-soluble nonionic, anionic or weakly cationic synthetic surfactant, (ii) a water-insoluble long chain fatty alcohol and (iii) an anionic surfactant which is either an alkali metal or alkanolamine soap or an alkyl or alkaryl sulphate, sulphonate or ether sulphate, or an N-acyl sarcosinate. Such compositions therefore contain as essential components two different types of surfactant, both of which are water-soluble or substantially water-soluble (i.e., self-dispersing) and a third insoluble ingredient namely the long chain fatty alcohol.

OBJECTS OF INVENTION

An object of this invention is to provide stable aerosol foam-forming emulsions having good foam forming properties and which are entirely soap-free. This is in contrast to the compositions disclosed in the aforesaid OLS in which the compositions do preferably contain a soap albeit in reduced amount. A further object is to provide stable aerosol foam-forming emulsions having good foaming properties and which are scum-free and have scum-dispersing properties when used in hard water.

SUMMARY OF INVENTION

The present invention is based on the discovery that certain selected nitrogen-containing surfactants, in particular, selected from the group consisting of water-soluble ethylene oxide adducts of long chain fatty acid amides, long chain alkylamine oxides, lauric polyamide, oxyethyl alkyl ammonium phosphates, and quaternary ammonium salts of long chain alkylamines, when used in combination with a water-insoluble long chain fatty alcohol, particularly tetradecanol (myristyl alcohol) and a third surfactant component give rise to aerosol emulsions of considerable stability even at the moderately elevated temperatures referred to above. In this connection, it should be mentioned that the term "stability" is being used in a somewhat wider sense that that which is normally associated with the phrase "a stable emulsion." Where used in this specification in relation to emulsions, "stable" is to be taken to include not only cases where there is little or no phase separation on standing, but also cases where there may be phase separation when the emulsion is left to stand for any length of time provided that the emulsion can easily be re-established by a few shakes of the hand.

DETAILED DESCRIPTION

In accordance with this invention there is provided an aerosol foam dispenser comprising a pressurized container equipped with a dispensing head and manually operable valve, and containing an aqueous soap-free surfactant concentrate, and emulsified or readily emulsifiable therewith, a normally gaseous aerosol propellant in liquid phase, said concentrate consisting essentially of water and;

(i) from 1–15% by weight of the concentrate, preferably 3–8%, of a nitrogen-containing surfactant selected from:

(a) water-soluble ethylene oxide adducts of long chain fatty acid amides, being adducts of the formula:

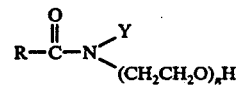

where
R is a straight chain $C_{12}$–$C_{18}$ alkyl group;
Y is H or $(CH_2CH_2O)_mH$, where $m$ is an integer of from 1–30;
$n$ is an integer of from 1–30; and the total of $n + m$ is from 1–40; and with the proviso that, when Y is H, then $n$ is greater than 10;

(b) long chain alkyl group-containing amine oxides of the formula:

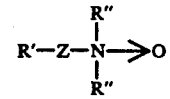

where
R' is a straight chain $C_{11}$–$C_{17}$ alkyl group;
each R" is $C_1$–$C_3$ alkyl; and
Z is $CH_2$ or $CH_2CONH(CH_2)_x$—, where $x$ is an integer of from 2–5;

(c) quaternary ammonium salts of the formula:

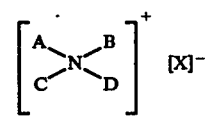

where
A is a straight chain $C_{12}$–$C_{18}$ alkyl group, X is an anion, e.g., $Cl^-$ or $Br^-$, and B, C and D represent one of the following combinations:
(i) B, C and D are each separate $C_1$–$C_3$ alkyl groups;
(ii) B and C are each $(CH_2CH_2O)_y$, where $y$ is an integer with B and C together providing a total of 2–12 ethoxy units and D is $C_1$–$C_3$ alkyl; and
(iii) B, C and D together with the nitrogen atom to which they are attached jointly represent a pyridine nucleus;

(d) a water-dispersible lauric polyamide (2:1), having a melting point in the range 53°–57° C., an acid number not greater than 10 and an alkali number in the range 136–156; and (e) a tris-(polyoxyethylene) alkyl ammonium phosphate of the formula

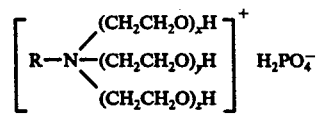

where R is a straight chain $C_{12}-C_{18}$ alkyl group and $x$, $y$ and $z$ are integers of from 1-20.
  (ii) from 0.5-6% by weight based on the concentrate, preferably 1-3%, of a long chain fatty alcohol, preferably tetradecanol; and
  (iii) from 1-15% by weight based on the concentrate, preferably 2-8%, of (a) a water-soluble or insoluble synthetic nonionic surfactant having an HLB value of from 3-40 and containing, as its hydrophobic part a straight chain alkyl group of from 12-18 carbon atoms or an alkaryl group containing a straight chain alkyl substituent of from 5-12 carbon atoms, (b) a long chain alkyl or alkaryl sulphosuccinate or (c) an N-acyl-N-alkyl taurate, the weight ratio of components (i) and (iii) together to component (ii) being from 0.5:1 to 12:1, preferably 2:1 to 6:1, and the three components of the concentrate being such that the HLB value is from 8-18.

Throughout this specification the expression "long chain" when used in expressions such as "long chain fatty acid," "long chain fatty alcohol," "long chain alkyl" is intended to cover straight chain groups containing from 12-18 carbon atoms, whilst the expression "long chain alkaryl" is intended to cover alkyl-substituted aryl groups comprising a benzene or naphthalene nucleus substituted by a straight chain $C_5-C_{12}$ alkyl substituent. It is also to be understood that, as is customary in referring to surfactants, phrases specifying a carbon atom range, e.g., $C_{12}-C_{18}$, or a specific number of carbon atoms, e.g., $C_{12}$ alkyl, when referring to a surfactant component are intended to cover mixtures of compounds in which the alkyl substituents are predominantly within the stated range, or are predominantly alkyl groups having that particular number of carbon atoms, but which may contain small amounts of other compounds in which the alkyl groups are outside the stated range or which may contain unsaturated, e.g., alkenyl, groups, the reason being, of course, that in practice, such surfactants are frequently obtained from natural products, e.g., coconut oil, which are themselves mixtures of compounds of different chain length, but with one or a small range of chain lengths predominating.

The surfactants used in the present invention both as components (i) and (iii) are all commercially available materials.

Typical nitrogen-containing surfactants useful as the first component are:
  Myristyl dimethylamine oxide
  Coco polyoxyethylene (2) methyl ammonium chloride
  Coco diethanolamide
  Lauryl pyridinium chloride
  Tris(oxyethyl)cetyl ammonium phosphate
  Lauric diethanolamide.

The preferred surfactants for use as the third component of the compositions of the present invention are nonionic surfactants selected from alkylene (e.g., ethylene and/or propylene) oxide adducts of long chain fatty alcohols and acids, and of polyol esters of long chain fatty acids, and of $C_5-C_{12}$ alkyl phenols, and also polyol (e.g., sucrose) esters of long chain fatty acids. Also suitable are ethylene oxide adducts of long chain primary alkylamines containing more than 30 ethylene oxide units. Especially preferred are polyoxyethylene oxide adducts of long chain alcohols containing from 10-30 ethylene oxide units, nonyl phenoxypolyoxyethylene (50) ethanol and polyoxyethylene (20) sorbitan monostearate.

Suitable sulphosuccinate and taurates useful as the third component of the compositions of this invention in place of the nonionic surfactants discussed above are, for example disodium lauryl ether sulphosuccinate and N-(coconut oil acyl)-N-methyltaurine sodium salt.

Generally speaking the total solids concentration of the aqueous concentrates used in the present invention will be from 5-30% by weight, preferably 8-20%, by weight, based on the weight of the concentrate, but these amounts are not critical.

The propellants used in the compositions used in the present invention are conventional materials, e.g., hydrocarbon and hydrocarbon mixtures, e.g., the mixture of butane, isobutane and propane known commercially as Butane 40, and halohydrocarbons such as dichlorodifluoromethane (12) on its own or mixtures thereof with dichlorotetrafluoroethane (114). Mixtures of hydrocarbon and halohydrocarbon propellants may also be used. The quantity of propellant used will generally be in the range 3-12%, by weight of the total emulsion, depending on the propellant used, although the exact amount is by no means critical to this invention. Generally speaking, hydrocarbon propellants such as butane mixtures will be used in amounts at the lower end of the stated range, e.g., 3-7%, whilst halohydrocarbon propellants will be used in amounts at the upper end of the range, e.g., 7-12%. Generally preferred as propellants will be the halohydrocarbons, particularly fluorocarbons, and mixtures thereof with hydrocarbons. Hydrocarbon propellants on their own are less preferred.

Other ingredients such as antioxidants, perfuming agents, stabilizers, viscosity modifiers, humectants, emollients and lubricants, may be included in the compositions of this invention in minor amounts as is conventional in the art, and are embraced by the phrase "consisting essentially of."

Examples of aerosol shaving foam preparations according to the invention are as follows. Each composition was packaged in a conventional pressurised dispenser equipped with conventional discharge valve and foam dispensing head. In every case, a good stiff foam could be dispensed from the nozzle after shaking the dispenser in the hand for a few seconds before opening the valve. This ability was maintained even after the packages had been allowed to stand for prolonged periods of time at temperatures up to 40° C.

Typical foamable aerosol emulsions according to this invention are illustrated in Examples 1-9.

EXAMPLE 1

| | Wt.% |
|---|---|
| Myristyl dimethyl amine oxide | 5.50 |
| Polyethylene glycol (mol.wt.400) monolaurate | 1.00 |
| Myristyl alcohol | 2.02 |
| Glycerol | 4.50 |
| Distilled water | 78.58 |
| Propellant 12/114 (60:40) | 8.40 |

EXAMPLE 2

| | Wt.% |
|---|---|
| Coco polyoxyethylene (2) methyl ammonium chloride | 5.50 |
| Polyoxyethylene (20) cetyl ether | 4.58 |

-continued

| | Wt.% |
|---|---|
| Myristyl alcohol | 2.02 |
| Distilled water | 79.50 |
| Propellant (12/114 (60:40) | 8.40 |

EXAMPLE 3

| | wt.% |
|---|---|
| Coco diethanolamide | 0.92 |
| Polyoxyethylene (4) lauryl ether | 4.58 |
| Myristyl alcohol | 1.83 |
| Distilled water | 84.27 |
| Propellant 12/114 (60:40) | 8.40 |

EXAMPLE 4

| | Wt.% |
|---|---|
| Lauryl pyridinium chloride | 5.50 |
| Octyl phenylpolyoxyethylene (10) ethanol | 4.58 |
| Myristyl alcohol | 2.02 |
| Distilled water | 79.50 |
| Propellant 12/114 (60:40) | 8.40 |

EXAMPLE 5

| | Wt.% |
|---|---|
| Tris-(oxyethyl)cetyl ammonium phosphate | 2.75 |
| Polyoxyethylene (20) cethyl ether | 4.58 |
| Myristyl alcohol | 2.02 |
| Glycerol | 4.25 |
| Distilled water | 78.00 |
| Propellant 12/114 (60:40) | 8.40 |

EXAMPLE 6

| | Wt.% |
|---|---|
| Disodium lauryl ether sulphosuccinate | 4.58 |
| Lauric diethanolamide | 2.66 |
| Myristyl alcohol | 2.93 |
| Distilled water | 81.43 |
| Propellant 12/114 (60:40) | 8.40 |

EXAMPLE 7

| | Wt.% |
|---|---|
| Lauric polyamide (2:1) | 4.58 |
| Myristyl alcohol | 2.02 |
| Nonyl phenoxypolyoxyethylene (49) ethanol | 2.75 |
| Myristic acid | 0.46 |
| Distilled water | 81.79 |
| Propellant 12/114 (60:40) | 8.40 |

EXAMPLE 8

| | Wt.% |
|---|---|
| Tris-(oxyethyl)cetyl ammonium phosphate | 4.58 |
| Woolwax alcohol sodium sulphosuccinate | 4.58 |
| Myristyl alcohol | 2.02 |
| Distilled water | 80.42 |
| Propellant 12/114 (60:40) | 8.40 |

EXAMPLE 9

| | Wt.% |
|---|---|
| Lauric diethanolamide | 4.58 |
| N-(coconut oil acyl)-N-methyltaurine sodium salt | 2.2 |
| Myristyl alcohol | 2.2 |
| Distilled water | 82.62 |
| Propellant 12/114 (60:40) | 8.4 |

We claim:

1. An aerosol shaving foam dispenser containing an aqueous soap-free surfactant concentrate, and emulsified or readily emulsifiable therewith, a gaseous aerosol propellant in liquid phase, said concentrate consisting essentially of water and;
(i) from 1–15% by weight of the concentrate of a nitrogen-containing surfactant selected from the group consisting of:

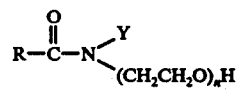

where
R is a straight chain $C_{12}$–$C_{18}$ alkyl group;
Y is H or $(CH_2CH_2O)_mH$, where $m$ is an integer of from 1–30;
$n$ is an integer of from 1–30; and
the total of $n + m$ is from 1–40;
and with the proviso that, when Y is H, then $n$ is greater than 10;

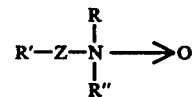

where
R' is a straight chain $C_{11}$–$C_{17}$ alkyl group;
R'' is $C_1$–$C_3$ alkyl; and
Z is $CH_2$ or $CH_2CONH(CH_2)_x$—, where $x$ is an integer of from 2–5; and

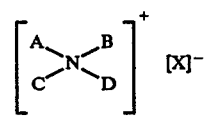

where A is a straight chain $C_{12}$–$C_{18}$ alkyl group, X is an anion and B, C, and D represent one of the following combinations:
(i) B, C and D are each separate $C_1$–$C_3$ alkyl groups;
(ii) B and C are each $(CH_2CH_2O)_y$, where $y$ is an integer with B and C together providing a total of 2–12 ethoxy units and D is $C_1$–$C_3$ alkyl; and
(iii) B, C and D together with the nitrogen atom to which they are attached jointly represent a pyridine nucleus; or
a water-dispersible lauric polyamide (2:1), having a melting point in the range 53°–57° C., an acid number not greater than 10 and an alkali number in the range 136–156; or
a tris-(polyoxyethylene) alkyl ammonium phosphate of the formula

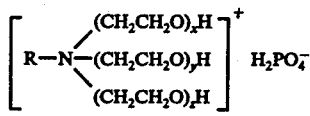

where R is a straight chain $C_{12}$–$C_{18}$ alkyl group and $x$, $y$ and $z$ are integers of from 1–20;

(ii) from 0.5–6% by weight based on the concentrate, of a long chain fatty alcohol containing from 12–18 carbon atoms; and (iii) from 1–15% by weight based on the concentrate of (a) a water-soluble or insoluble synthetic nonionic surfactant having an HLB value of from 3–40 and containing, as its hydrophobic part a straight chain alkyl group of from 12–18 carbon atoms or alkyl-substituted benzene or napphthalene group containing a straight chain alkyl substituent of from 5–12 carbon atoms, (b) a long chain alkyl sulphosuccinate containing from 12–18 carbon atoms in the alkyl group or a benzene or napthalene sulphosuccinate containing a straight chain alkyl substituent of from 5–12 carbon atoms on the aromatic nucleus, or (c) an N-coconut-acyl-N-methyl taurate, the weight ratio of components (i) and (iii) together to component (ii) being from 0.5:1 to 12:1 and the three components of the concentrate being such that the HLB value is from 8–18.

2. A dispenser according to claim 1, wherein the aqueous concentrate contains from 3–8% of the nitrogen containing surfactant, from 1–3% of long chain fatty alcohol and from 2–8% of the surfactant specified as component (iii), and wherein the weight ratio of components (i) and (iii) together to component (ii) is from 2:1 to 6:1.

3. A dispenser according to claim 1, wherein the long chain fatty alcohol is tetradecanol.

4. A dispenser according to claim 1, wherein component (iii) of the aqueous concentrate is an ethylene oxide adduct of a long chain fatty alcohol containing from 12–18 carbon atoms with from 10–30 moles of ethylene oxide, nonyl phenoxypolyoxyethylene (50) ethanol or polyoxyethylene (20) sorbitan monostearate.

5. A dispenser according to claim 1, wherein X is $Cl^-$ or $Br^-$.

* * * * *